US010065908B1

(12) United States Patent
Siedler et al.

(10) Patent No.: US 10,065,908 B1
(45) Date of Patent: Sep. 4, 2018

(54) ALKYLAROMATIC PROCESS WITH REMOVAL OF AROMATIC BY-PRODUCTS

(71) Applicant: UOP LLC, Des Plaines, IL (US)

(72) Inventors: Nathan A. Siedler, Hoffman Estates, IL (US); Charles P. Luebke, Mount Prospect, IL (US); Cynthia K. Zimmerman, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/635,996

(22) Filed: Jun. 28, 2017

(51) Int. Cl.
  *C07C 7/04* (2006.01)
  *B01D 3/14* (2006.01)
  *C07C 7/00* (2006.01)
  *C07C 7/12* (2006.01)

(52) U.S. Cl.
  CPC .............. *C07C 7/005* (2013.01); *B01D 3/143* (2013.01); *C07C 7/04* (2013.01); *C07C 7/12* (2013.01)

(58) Field of Classification Search
  CPC .. C07C 7/005; C07C 7/04; C07C 7/12; B01D 3/143
  See application file for complete search history.

(56) References Cited

U.S. PATENT DOCUMENTS

| 6,762,334 | B1 | 7/2004 | Stewart et al. |
| 9,026,252 | B2 | 5/2015 | Schaefer et al. |
| 9,079,811 | B2 | 7/2015 | Frey et al. |
| 9,328,037 | B2 | 5/2016 | Riley et al. |
| 2007/0203387 | A1* | 8/2007 | Glover ...................... C07C 2/66 585/831 |

FOREIGN PATENT DOCUMENTS

EP   1758839 B1   7/2009

* cited by examiner

*Primary Examiner* — Brian A McCaig
*Assistant Examiner* — Jason Y Chong

(57) ABSTRACT

Processes for removal of heavy aromatic compounds in an alkylated aromatic compounds production complex is disclosed. The processes includes separating a first component from a second component comprising introducing a feed stream comprising the second component and less than about 5 wt % of the first component to one or more top trays of a prefractionation column. The feed stream is separated in the prefractionation column to provide a prefractionation column overhead stream comprising at least about 50 wt % of the second component present in the feed stream and a prefractionation column bottoms stream. A first portion of the prefractionation columns bottom stream is vaporized by heat exchange with a low temperature fluid stream having a temperature of about 150-200° C. in a reboiler and passing the vaporized first portion through the prefractionation column.

19 Claims, 1 Drawing Sheet

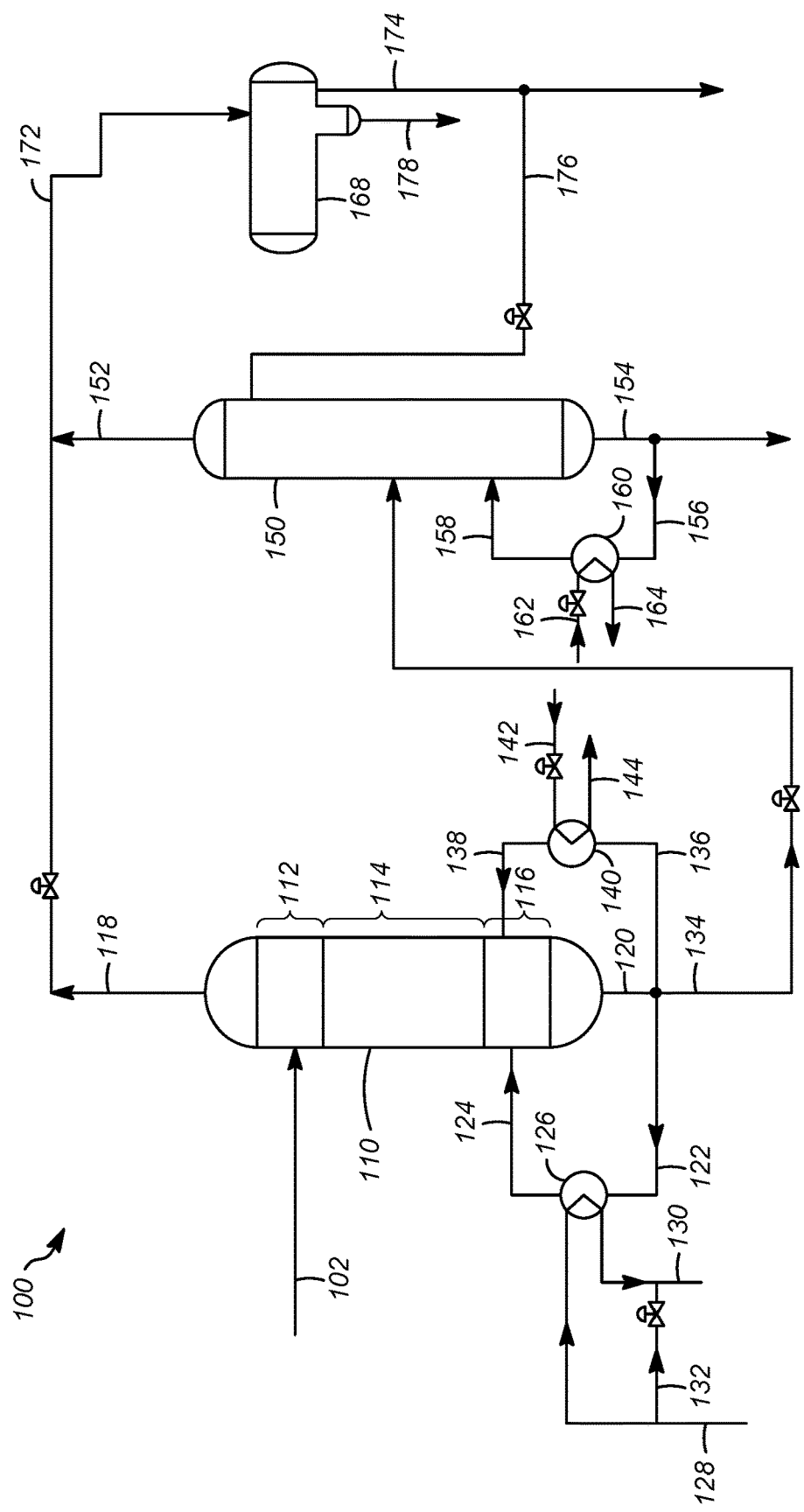

ALKYLAROMATIC PROCESS WITH REMOVAL OF AROMATIC BY-PRODUCTS

TECHNICAL FIELD

The technical field generally relates to processes for the production of alkylated aromatic compounds having energy efficient removal of heavy aromatic compounds.

BACKGROUND

The production of normal paraffins provides the ability for upgrading products from straight runs of hydrocarbon streams derived from crude oil fractionation. In particular, straight run kerosene is further processed to separate out normal paraffins for higher valued products, such as used in the production of linear alkylbenzenes (LAB). Normal paraffins in the range of $C_{10}$ to $C_{13}$ are important precursors to LAB production, which is in turn used to produce linear alkylbenzene sulfonate (LAS). LAS is the predominant surfactant used in the production of detergents.

The large utility of detergents and other cleaners has led to extensive development in the areas of detergent production and formulation. While detergents can be formulated from a wide variety of different compounds much of the world's supply is formulated from chemicals derived from alkylbenzenes. The compounds are produced in petrochemical complexes in which an aromatic hydrocarbon, typically benzene, is alkylated with an olefin of the desired structure and carbon number for the side chain. Typically the olefin is actually a mixture of different olefins forming a homologous series having a range of three to five carbon numbers. The olefin(s) can be derived from several alternative sources. For instance, they can be derived from the oligomerization of propylene or butenes or from the polymerization of ethylene. Economics has led to the production of olefins by the dehydrogenation of the corresponding paraffin being the preferred route to produce the olefin.

The choice of carbon numbers is set by the boiling point range of straight run cuts from crude distillation. Kerosene boiling range fractions from crude oil provide heavier paraffins. Paraffins having 8 to 15 carbons are present in significant concentrations in relatively low cost kerosene. These paraffins have been a predominant source for linear alkanes and the leading source of olefin precursors for use in making LABs. Recovery of the desired normal paraffins from kerosene is performed by adsorption separation, which is one process in overall production of LABs. The paraffins are then passed through a catalytic dehydrogenation zone wherein some of the paraffins are converted to olefins. However, the paraffin dehydrogenation also generates heavy aromatics which are undesirable. Thereafter, the resulting effluent from the paraffin dehydrogenation zone is passed through an aromatic removal zone for selective removal of aromatics before passing the feed to the downstream alkylation zone in which the olefins are reacted with the aromatic substrate.

Typically, the aromatics removal zone in the LAB production process, includes a plurality of adsorbers along with a desorbent column. The plurality of adsorbers are regenerated subsequent to adsorption using a regenerant stream such as a benzene stream. In the desorbent column, heavy aromatics are removed from the spent regenerant stream comprising the heavy aromatics. Currently, the desorbent column require a large amount of hot oil duty to reboil desorbent benzene in order to remove a small amount of heavy aromatics. Typically, less than 10% of the desorbent column feed is taken out as a bottoms stream, which causes unreasonable product split and issues in column design.

Accordingly, it is desirable to provide an improved process for separation of heavy aromatics from a spent regenerant stream. It is desirable for the instant process to have reasonable product split for the desorbent column. It is also desirable to minimize hot oil duty required in fractionating the heavy aromatics in the spent regenerant stream in such apparatuses. Other desirable features and characteristics of the present subject matter will become apparent from the subsequent detailed description of the subject matter and the appended claims, taken in conjunction with the accompanying drawing and this background of the subject matter.

BRIEF SUMMARY

Various embodiments contemplated herein relate to processes for the production of alkylated aromatic compounds. The exemplary embodiments taught herein illustrate an apparatus and processes for production of alkylated aromatic compounds having an energy efficient process for removal of heavy aromatic compounds.

In accordance with an exemplary embodiment, a process is provided for separating a first component from a second component comprising introducing a feed stream comprising the second component and less than about 5 wt % of the first component to one or more top trays of a prefractionation column. The feed stream is separated in the prefractionation column to provide a prefractionation column overhead stream comprising at least about 50 wt % of the second component present in the feed stream and a prefractionation column bottoms stream. A first portion of the prefractionation columns bottom stream is vaporized by heat exchange with a low temperature fluid stream having a temperature of about 150-200° C. in a reboiler and passing the vaporized first portion through the prefractionation column. A second portion of the prefractionation column bottoms stream is separated in a fractionation column to provide a fractionation column overhead stream rich in the second component and a fractionation column bottoms stream rich in the first component.

In accordance with another exemplary embodiment, a process is provided for separating $C_{7+}$ aromatics from a spent regenerant stream comprising introducing the spent regenerant stream to one or more top trays of a prefractionation column, the spent regenerant stream comprising regenerant and less than about 5 wt % $C_{7+}$ aromatics. The spent regenerant stream in the prefractionation column is separated to provide a prefractionation column overhead stream comprising at least about 50 wt % of the regenerant present in the spent regenerant stream and a prefractionation column bottoms stream comprising the $C_{7+}$ aromatics. A first portion of the prefractionation columns bottom stream is vaporized by heat exchange with a low temperature fluid stream having a temperature of about 150-200° C. in a reboiler and the vaporized first portion is passed to the prefractionation column. A second portion of the prefractionation column bottoms stream is separated in a desorbent column to provide a desorbent column overhead stream rich in the regenerant and a desorbent column bottoms stream rich in the $C_{7+}$ aromatics.

In accordance with yet another exemplary embodiment, a process is provided for separating of $C_{7+}$ aromatics from a spent regenerant stream comprising introducing the spent regenerant stream to one or more top trays of a prefractionation column, the spent regenerant stream comprising regenerant and less than about 5 wt % $C_{7+}$ aromatics. The spent regenerant stream is separated in the prefractionation column at an operating pressure to provide a prefractionation column overhead stream comprising at least about 50 wt % of the regenerant present in the spent regenerant stream and a prefractionation column bottoms stream comprising $C_{7+}$ aromatics and remaining of the regenerant. An amount of the $C_{7+}$ aromatics in the prefractionation column overhead stream is controlled by measuring the concentration of $C_{7+}$ aromatics in the prefractionation column using an analyzer and a processor and changing the operating pressure of the prefractionation column. A first portion of the prefractionation columns bottom stream is vaporized by heat exchange with a low temperature fluid stream having a temperature of about 150-200° C. and the vaporized first portion is passed to the prefractionation column. A second portion of the prefractionation column bottoms stream is separated in a desorbent column to provide a desorbent column overhead stream rich in the regenerant and a desorbent column bottoms stream rich in the $C_{7+}$ aromatics These and other features, aspects, and advantages of the present disclosure will become better understood upon consideration of the following detailed description, drawing and appended claims.

BRIEF DESCRIPTION OF THE DRAWING

The various embodiments will hereinafter be described in conjunction with the following FIGURE, wherein like numerals denote like elements.

The FIGURE illustrates a process and apparatus for removal of heavy aromatic compounds according to an embodiment of the present disclosure.

Skilled artisans will appreciate that elements in the FIGURE are illustrated for simplicity and clarity and have not necessarily been drawn to scale. For example, the dimensions of some of the elements in the FIGURE may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, carbon dioxide, carbon monoxide, and sulfur and nitrogen compounds. Each of the above may also include aromatic and non-aromatic hydrocarbons.

As used herein, the term "zone" or "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "rich" or "purified" can mean an amount of at least generally 50%, preferably 70%, and more preferably 90% by mole, of a compound or class of compounds in a stream As depicted, process flow lines in the FIGURE can be referred to interchangeably as, e.g., lines, pipes, feeds, gases, products, discharges, parts, portions, or streams.

The term "communication" means that material flow is operatively permitted between enumerated components.

The term "passing" means that the material passes from a conduit or vessel to an object.

Olefins for use in the production of linear alkylbenzenes (LABs) are generated by dehydrogenation of paraffins to produce an olefins feed stream. The paraffins may be obtained from various sources including, but not limited to, from an adsorptive separation process, an oligomerization process, or produced from a renewable feedstock. The paraffin dehydrogenation process for the production of olefins generates aromatics. The aromatics include heavy aromatics that comprise aromatics with 7 or more carbons i.e. $C_{7+}$ aromatics. The heavy aromatics are impurities that affect the quality of the LAB product and performance of downstream units and need to be removed before the alkylation step.

Currently, the process for the removal of heavy aromatics from an olefin feed stream, before passing the olefin feed stream to an alkylation unit includes a two unit adsorbent system. A first adsorbent unit of the two unit adsorbent system generates a first adsorbent effluent stream with reduced heavy aromatics content. The first adsorbent unit effluent stream with reduced heavy aromatics is passed to a benzene alkylation unit. The first adsorbent unit is run until breakthrough. At breakthrough, the pressure of a second adsorbent unit is equalized with the pressure of the first adsorbent unit. The olefins feed stream is switched from the first adsorbent unit to the second adsorbent unit to generate a second adsorbent unit effluent stream. Breakthrough is determined by an analyzer disposed on the effluent from the absorbent unit to determine when the heavy aromatics content is exceeding a preset level. The analyzers may be used to adjust the timers to prevent breakthrough.

The second adsorbent bed effluent stream initially comprises a displacement fluid in the second adsorbent bed. The second adsorbent unit effluent stream is passed to the first adsorbent unit, displacing the residual first adsorbent unit fluid. Upon displacing the residual first adsorbent unit fluid, the displacement of the first adsorbent unit is discontinued, and the second adsorbent unit effluent stream is now on-line. The second adsorbent unit effluent stream is passed to the benzene alkylation unit. A regenerant is passed to the first adsorbent unit to regenerate the first adsorbent unit. The regenerant may have either a co-current or countercurrent flow through the first adsorbent unit as the olefins feed stream. When the first adsorbent unit is regenerated it is placed on stand-by.

The process continues with flow through the second adsorbent unit to generate the second adsorbent unit effluent stream. When the second adsorbent unit is near breakthrough, the pressure in the first adsorbent unit is equalized to the pressure in the second adsorbent unit. The olefins feed stream is switched to the first adsorbent unit, and the first adsorbent unit effluent stream is passed to the second adsorbent unit, displacing the second adsorbent unit fluid. Upon displacing the regenerant in the first adsorbent unit, the passing of the first adsorbent unit effluent stream to the second adsorbent unit is discontinued. The first adsorbent unit effluent stream is now passed to the benzene alkylation unit. The process completes the cycle by passing the regenerant to the second adsorbent unit to regenerate the second adsorbent unit. The regenerant may have either a co-current or countercurrent flow through the second adsorbent unit in the same direction as the olefins feed stream. A preferred regenerant is benzene. In an embodiment, n-pentane may be used as a purge stream. The regenerant obtained from the adsorbent units during regeneration is a spent regenerant stream and may be contaminated with $C_{7+}$ aromatics and is passed to a process and apparatus 100 may be processed further as illustrated in the FIGURE.

The process can further include the use of a trim adsorbent unit. The trim adsorbent unit is a smaller adsorbent unit and is used to finish up the displacement of the end of an adsorbent unit during the displacement step. At the end of the displacement step, the effluent stream from the adsorbent unit having the fluid displaced from the adsorbent unit is passed to the trim adsorbent unit to adsorb residual heavy aromatics from the adsorbent unit. The effluent from the trim displacement unit is passed to the benzene alkylation unit. After the first, or second, adsorbent unit is placed on line, the trim bed is regenerated with the regenerant.

Alternatively, another process utilizing a six bed adsorption system may be used for the removal of heavy aromatics from an olefin feed stream, before passing the olefin feed stream to the alkylation unit. The instant process utilizes six adsorbers with four on-line in a parallel configuration. The other two adsorbers are in various stages of regeneration providing a spent regenerant stream comprising the heavy aromatics which can be processed further as illustrated in the FIGURE.

The process and apparatus 100 for separating the heavy aromatics from the spent regenerant stream can be seen in the FIGURE including a prefractionation column 110 and a fractionation column 150. Although only two methods of obtaining spent regenerant stream have been described above, however, the present subject matter is not limited to above methods, and covers any suitable improvement or variation of the above disclosed methods to obtain the spent regenerant stream. In accordance with an exemplary embodiment as discussed, the fractionation column may a desorbent column and may be interchangeably referred to as the desorbent column 110. A spent regenerant stream in line 102 may be introduced to the prefractionation column 110. The spent regenerant stream in line 102 may include $C_{7+}$ aromatics as contaminants in addition to the regenerant. Although the instant embodiment has been described with respect to $C_{7+}$ aromatics being present as contaminants in the regenerant, however, the present disclosure in not limited to, and can be extended to separating any contaminant in a feedstream. In accordance with an exemplary embodiment, the amount of $C_{7+}$ aromatics present in the spent regenerant stream 102 may be less than about 5 wt. %, or less than about 2 wt %, or less than about 1 wt. %.

The prefractionation column 110 may include one or more top trays, one or more intermediate trays and one or more bottom trays. The one or more top trays may be present in top zone 112, the one or more intermediate trays may be present in the intermediate zone 114 and the one or more bottom trays may be present in the bottom zone 116. In accordance with an exemplary embodiment as shown in the FIGURE, the spent regenerant stream in line 102 may be introduced to the top zone 112 including the one or more top trays. In an aspect, the spent regenerant stream may be introduced to the top tray of the prefractionation column 110. The spent regenerant stream in line 102 may be separated in the prefractionation column 110 to provide a prefractionation column overhead stream in line 118 comprising at least about 50 wt % of the regenerant present in the spent regenerant stream and a prefractionation column bottoms stream in line 120. In accordance with an exemplary embodiment, at least about 70 wt % of the regenerant present in the spent regenerant stream may be separated into the prefractionation column overhead stream. In accordance with another exemplary embodiment, at least about 80 wt % of the regenerant present in the spent regenerant stream may be separated into the prefractionation column overhead stream. In accordance with yet exemplary embodiment, at least about 90 wt % of the regenerant present in the spent regenerant stream may separated into the prefractionation column overhead stream. In accordance with yet exemplary embodiment, the prefractionation column overhead stream may comprise up to about 95 wt % of the regenerant present in the spent regenerant stream. The prefractionation column bottoms stream may include the $C_{7+}$ aromatics and remaining of the regenerant. In accordance with an exemplary embodiment as shown in the FIGURE, there may no reflux in the prefractionation column 110. Accordingly, the prefractionation column may be interchangeably referred to as the non-refluxing prefractionation column 110.

The prefractionation column 110 may have an operating pressure from about 100 to about 210 kPa. In accordance with an exemplary embodiment, an amount of the $C_{7+}$ aromatics in the prefractionation column overhead stream may be controlled by varying the operating pressure of the prefractionation column 110. As shown, a pressure control valve on line 118 may be used to vary the operating pressure of the prefractionation column 110. In an aspect, an analyzer on prefractionation column overhead line 118 may be used to measure the amount of $C_{7+}$ aromatics in the prefractionation column overhead stream. In an embodiment, when the amount of $C_{7+}$ aromatics exceed a predetermined amount, the operating pressure of the prefractionation column 110 may be adjusted to effect a change in the amount of $C_{7+}$ aromatics in the prefractionation column overhead stream to an amount below the predetermined amount. In an aspect, the operating pressure may be adjusted using a control system. The control system may include a processor and any suitable structure for interacting with one or more sensors and controlling one or more actuators. The control system could, for example, represent a multivariable controller, such as a [Robust Multivariable Predictive Control Technology (RMPCT)] controller or other type of controller implementing [model predictive control (MPC)] or other [advanced predictive control (APC)]. As a particular example, each controller could represent a computing device running a real-time operating system. In an aspect, the control system may include one or more sensors, wherein the one or more sensors measure the amount of $C_{7+}$ in the prefractionation column overhead stream. Further, one or more process conditions including operating pressure of the prefractionation column 110 may be changed in response to the measured amount of $C_{7+}$ aromatics in the prefractionation column overhead stream. In an aspect, the one or more process conditions may be adjusted using a feedback module present in the control system. In an embodiment, the amount of amount of the $C_{7+}$ aromatics in the prefractionation column overhead stream may be controlled by controlling heat duty of the reboiler 126, as described below.

Turning to the prefractionation columns bottom stream in line 120, a first portion of the prefractionation columns bottom stream in line 122 may be heat exchanged in a reboiler 126 with a low temperature fluid stream in line 128 having a temperature of about 150-200° C. to provide a vaporized first portion in line 124. The low temperature fluid stream can be obtained from a variety of sources. It is an advantage to use the low temperature fluid streams as they are available abundantly and at a cheaper cost from various parts of the plant as compared to high temperature streams. In accordance with an exemplary embodiment, the low temperature fluid stream may be a selective dehydrogenation zone stripper bottoms stream. The vaporized first portion in line 124 may be passed to the prefractionation column 110. In accordance with an exemplary embodiment, the amount of the low temperature fluid stream used in the heat exchange may be controlled using a flow controller. The amount of heat exchange with the low temperature fluid stream may be used to control the amount of the $C_{7+}$ aromatics in the prefractionation column overhead stream. Accordingly, the heat duty of the reboiler 126 may be used to control the amount of the $C_{7+}$ aromatics in the prefractionation column overhead stream. In accordance with an exemplary embodiment as shown in the FIGURE, a valve on a bypass line 132 may be used to control the amount of the low temperature fluid stream being passed to the reboiler 126. Accordingly, a portion of the low temperature fluid stream may be bypassed around the reboiler 126 and may be withdrawn through the bypass line 132. A cooled low temperature fluid stream in line 130 may be withdrawn from the reboiler 126.

A second portion of the prefractionation column bottoms stream in line 134 may be passed to the desorbent column 150. Further, the process may include a startup-reboiler 140, which provides the required heat during start-up by heat exchanging a third portion of the prefractionation column bottoms stream in line 136 with a hot oil stream in line 142 having a temperature of about 400 to about 500° C. In addition to during start-up, the start-up reboiler 140 may be used when the low temperature fluid steam in not available in an amount to continuously provide the vaporized first portion to the prefractionation column 110. In such an event, a valve on the hot oil stream in line 142 may be open and a vaporized hot oil stream in line 138 may be provided to the prefractionation column 110. A spent hot oil stream may be withdrawn in line 144. Alternatively, in cases where the low temperature fluid steam may be available in sufficient volume, the valve on the hot oil stream in line 142 may be kept closed after the start-up.

The second portion of the prefractionation column bottoms stream in line 134 may be passed to the desorbent column 150. The desorbent column 150 may have an operating pressure from about 25 to about 35 kPa. In the desorbent column 150, a desorbent column overhead stream in line 152 rich in the regenerant may be separated from a desorbent column bottoms stream in line 154 rich in the $C_{7+}$ aromatics. A portion of the desorbent column bottoms stream in line 156 may be withdrawn and heat exchanged with a hot oil stream in line 162 to provide a vaporized portion of the desorbent columns bottom stream in line 158. The vaporized portion in line 158 may be passed to the desorbent column 150. A spent hot oil stream may be withdrawn in line 164.

The prefractionation column overhead stream in line 118 and the desorbent column overhead stream in line 152 may be passed to a desorbent column overhead system 168. The desorbent column overhead system 168 may comprise a desorbent column overhead condenser and a desorbent column overhead receiver. As shown, the prefractionation column 110 and the desorbent column 150 share a single overhead system. A benzene make-up stream (not shown) may also be provided to the desorbent column overhead system 168. In accordance with an exemplary embodiment as shown in the FIGURE, the prefractionation column overhead stream and the desorbent column overhead stream may be mixed to provide a desorbent column overhead system feed stream in line 172 which may be subsequently provided to the desorbent column overhead system 168. In operation, the desorbent column overhead system feed stream is passed to the desorbent column overhead condenser before being passed to the desorbent column overhead receiver. The desorbent column overhead system feed stream in line 172 may be condensed in the desorbent column overhead condenser and separated in the desorbent column overhead receiver.

A liquid regenerant stream in line 174 may be withdrawn from the desorbent column overhead system 168. A portion of the liquid regenerant stream may be withdrawn in line 176 and passed to the desorbent column 150 as reflux. Another portion of the liquid regenerant stream may be withdrawn as a drag stream (not shown). Steam condensate may be removed from system 168 in line 178.

In the conventional scheme, the desorbent column required a large amount of hot oil duty to reboil spent regenerant stream in order to remove a small amount of heavy aromatics from the spent regenerant stream. The apparatus and process as disclosed in the present disclosure allows using a low temperature fluid stream having a temperature of about 150° C. to 200° C. to fractionate a majority of the regenerant in the prefractionation column, instead of the hot oil stream having a temperature of about 350° C. to 400° C., thereby greatly reducing the hot oil duty. Further, as majority of the regenerant is removed in the prefractionation column overhead stream, the desorbent column can be a much smaller column and has a more reasonable product split with 90% being the overhead stream and 10% as the bottoms stream. Moreover, the hot oil duty associated with the desorbent column is also greatly reduced.

In some embodiments, various functions described herein are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD),Blu-ray or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

SPECIFIC EMBODIMENTS

While the following is described in conjunction with specific embodiments, it will be understood that this description is intended to illustrate and not limit the scope of the preceding description and the appended claims.

A first embodiment of the invention is a process for separating a first component from a second component comprising introducing a feed stream comprising the second component and less than about 5 wt % of the first component to one or more top trays of a prefractionation column; separating the feed stream in the prefractionation column to provide a prefractionation column overhead stream comprising at least about 50 wt % of the second component present in the feed stream and a prefractionation column bottoms stream; vaporizing a first portion of the prefractionation columns bottom stream by heat exchange with a low temperature fluid stream having a temperature of about 150-200° C. in a reboiler and passing the vaporized first portion through the prefractionation column; and separating a second portion of the prefractionation column bottoms stream in a fractionation column to provide a fractionation column overhead stream rich in the second component and a fractionation column bottoms stream rich in the first component. An embodiment of the invention is one, any or all of prior embodiments in this paragraph up through the first embodiment in this paragraph, wherein the prefractionation column is operated at a pressure equal to or higher that the operating pressure of the fractionation column. An embodiment of the invention is one, any or all of prior embodiments in this paragraph up through the first embodiment in this paragraph, wherein at least about 70 wt % of the second component present in the feed stream is separated into the prefractionation column overhead stream. An embodiment of the invention is one, any or all of prior embodiments in this paragraph up through the first embodiment in this paragraph, wherein the low temperature fluid stream is a selective dehydrogenation zone stripper bottoms stream. An embodiment of the invention is one, any or all of prior embodiments in this paragraph up through the first embodiment in this paragraph further comprising controlling an amount of the first component in the prefractionation column overhead stream by varying an operating pressure of the prefractionation column. An embodiment of the invention is one, any or all of prior embodiments in this paragraph up through the first embodiment in this paragraph, wherein the amount of first component in the prefractionation column overhead is detected using an analyzer. An embodiment of the invention is one, any or all of prior embodiments in this paragraph up through the first embodiment in this paragraph, wherein the prefractionation column overhead stream and the fractionation column overhead stream are passed to a fractionation column overhead system.

A second embodiment of the invention is a process for separating $C_{7+}$ aromatics from a spent regenerant stream, the process comprising introducing the spent regenerant stream to one or more top trays of a prefractionation column, the spent regenerant stream comprising regenerant and less than about 5 wt % $C_{7+}$ aromatics; separating the spent regenerant stream in the prefractionation column to provide a prefractionation column overhead stream comprising at least about 50 wt % of the regenerant present in the spent regenerant stream and a prefractionation column bottoms stream comprising the $C_{7+}$ aromatics; vaporizing a first portion of the prefractionation columns bottom stream by heat exchange with a low temperature fluid stream having a temperature of about 150-200° C. in a reboiler and passing the vaporized first portion to the prefractionation column; and separating a second portion of the prefractionation column bottoms stream in a desorbent column to provide a desorbent column overhead stream rich in the regenerant and a desorbent column bottoms stream rich in the $C_{7+}$ aromatics. An embodiment of the invention is one, any or all of prior embodiments in this paragraph up through the second embodiment in this paragraph, wherein the prefractionation column is operated at a pressure of from about 100 to about 210 kPa. An embodiment of the invention is one, any or all of prior embodiments in this paragraph up through the second embodiment in this paragraph, wherein at least about 70 wt % of the regenerant present in the spent regenerant stream is separated into the prefractionation column overhead stream. An embodiment of the invention is one, any or all of prior embodiments in this paragraph up through the second embodiment in this paragraph, wherein the low temperature fluid stream is a selective dehydrogenation zone stripper bottoms stream. An embodiment of the invention is one, any or all of prior embodiments in this paragraph up through the second embodiment in this paragraph further comprising controlling an amount of the $C_{7+}$ aromatics in the prefractionation column overhead stream by varying an operating pressure of the prefractionation column. An embodiment of the invention is one, any or all of prior embodiments in this paragraph up through the second embodiment in this paragraph, wherein the amount of $C_{7+}$ aromatics in the prefractionation column overhead is detected using an analyzer. An embodiment of the invention is one, any or all of prior embodiments in this paragraph up through the second embodiment in this paragraph wherein the desorbent column is operated at a pressure of from about 25 kPa to about 35 kPa. An embodiment of the invention is one, any or all of prior embodiments in this paragraph up through the second embodiment in this paragraph, wherein the prefractionation column overhead stream and the desorbent column overhead stream are passed to a desorbent column overhead system. An embodiment of the invention is one, any or all of prior embodiments in this paragraph up through the second embodiment in this paragraph, wherein the regenerant is benzene.

A third embodiment of the invention is a process for separating of $C_{7+}$ aromatics from a spent regenerant stream comprising introducing the spent regenerant stream to one or more top trays of a prefractionation column, the spent regenerant stream comprising regenerant and less than about 5 wt % $C_{7+}$ aromatics; separating the spent regenerant stream in the prefractionation column at an operating pressure to provide a prefractionation column overhead stream comprising at least about 50 wt % of the regenerant present in the spent regenerant stream and a prefractionation column bottoms stream comprising $C_{7+}$ aromatics and remaining of the regenerant; controlling an amount of the $C_{7+}$ aromatics in the prefractionation column overhead stream by measuring the concentration of $C_{7+}$ aromatics in the prefractionation column using an analyzer and changing the operating pressure of the prefractionation column; vaporizing a first portion of the prefractionation columns bottom stream by heat exchange with a low temperature fluid stream having a temperature of about 150-200° C. and passing the vaporized first portion to the prefractionation column; and separating a second portion of the prefractionation column bottoms stream in a desorbent column to provide a desorbent column overhead stream rich in the regenerant and a desorbent column bottoms stream rich in the $C_{7+}$ aromatics. An embodiment of the invention is one, any or all of prior embodiments in this paragraph up through the third embodiment in this paragraph, wherein the prefractionation column is operated at a pressure of from about 100 to about 210 kPa. An embodiment of the invention is one, any or all of prior embodiments in this paragraph up through the third embodiment in this paragraph, wherein at least about 70 wt % of the regenerant present in the spent regenerant stream is separated into the prefractionation column overhead stream. An embodiment of the invention is one, any or all of prior embodiments in this paragraph up through the third embodiment in this paragraph, wherein the low temperature fluid stream is a selective dehydrogenation zone stripper bottoms stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated. In the foregoing, all temperatures are set forth in degrees Celsius and, all parts and percentages are by weight, unless otherwise indicated.

The invention claimed is:

1. A process for separating $C_{7+}$ aromatics from benzene comprising:
   (a) introducing a feed stream comprising benzene and less than about 5 wt % of $C_{7+}$ aromatics to the top tray of a prefractionation column;
   (b) separating the feed stream in the prefractionation column to provide a prefractionation column overhead stream comprising at least about 50 wt % of benzene present in the feed stream and a prefractionation column bottoms stream;
   (c) vaporizing a first portion of the prefractionation columns bottoms stream by heat exchange with a low temperature fluid stream having a temperature of about 150-200° C. in a reboiler and passing the vaporized first portion through the prefractionation column; and
   (d) separating a second portion of the prefractionation column bottoms stream in a fractionation column to provide a fractionation column overhead stream rich in benzene and a fractionation column bottoms stream rich in $C_{7+}$ aromatics.

2. The process of claim 1, wherein the prefractionation column is operated at a pressure equal to or higher than an operating pressure of the fractionation column.

3. The process of claim 1, wherein at least about 70 wt % of benzene present in the feed stream is separated into the prefractionation column overhead stream.

4. The process of claim 1, wherein the low temperature fluid stream is a selective dehydrogenation zone stripper bottoms stream.

5. The process of claim 1 further comprising controlling an amount of $C_{7+}$ aromatics in the prefractionation column overhead stream by varying an operating pressure of the prefractionation column.

6. The process of claim 5, wherein the amount of $C_{7+}$ aromatics in the prefractionation column overhead is detected.

7. The process of claim 1, wherein the prefractionation column overhead stream and the fractionation column overhead stream are passed to a fractionation column overhead system.

8. A process for separating $C_{7+}$ aromatics from a spent regenerant stream, the process comprising:
   (a) introducing the spent regenerant stream to the top tray of a prefractionation column, the spent regenerant stream comprising benzene and less than about 5 wt % $C_{7+}$ aromatics;
   (b) separating the regenerant stream in the prefractionation column to provide a prefractionation column overhead stream comprising at least about 50 wt % of benzene present in the spent regenerant stream and a prefractionation column bottoms stream comprising the $C_{7+}$ aromatics;
   (c) vaporizing a first portion of the prefractionation columns bottoms stream by heat exchange with a low temperature fluid stream having a temperature of about 150-200° C. in a reboiler and passing the vaporized first portion to the prefractionation column; and
   (d) separating a second portion of the prefractionation column bottoms stream in a desorbent column to provide a desorbent column overhead stream rich in benzene and a desorbent column bottoms stream rich in the $C_{7+}$ aromatics.

9. The process of claim 8, wherein the prefractionation column is operated at a pressure of from about 100 to about 210 kPa.

10. The process of claim 8, wherein at least about 70 wt % of benzene present in the spent regenerant stream is separated into the prefractionation column overhead stream.

11. The process of claim 8, wherein the low temperature fluid stream is a selective dehydrogenation zone stripper bottoms stream.

12. The process of claim 8 further comprising controlling an amount of the $C_{7+}$ aromatics in the prefractionation column overhead stream by varying an operating pressure of the prefractionation column.

13. The process of claim 12, wherein the amount of $C_{7+}$ aromatics in the prefractionation column overhead is detected.

14. The process of claim 8, wherein the desorbent column is operated at a pressure of from about 25 kPa to about 35 kPa.

15. The process of claim 8, wherein the prefractionation column overhead stream and the desorbent column overhead stream are passed to a desorbent column overhead system.

16. A process for separating of $C_{7+}$ aromatics from a spent regenerant stream comprising:
   (a) introducing the spent regenerant stream to the top tray of a prefractionation column, the spent regenerant stream comprising benzene and less than about 5 wt % $C_{7+}$ aromatics;
   (b) separating the regenerant stream in the prefractionation column at an operating pressure to provide a prefractionation column overhead stream comprising at least about 50 wt % of benzene present in the spent regenerant stream and a prefractionation column bottoms stream comprising $C_{7+}$ aromatics and remaining of benzene;
   (c) controlling an amount of the $C_{7+}$ aromatics in the prefractionation column overhead stream by measuring the concentration of $C_{7+}$ aromatics in the prefractionation column overhead and changing the operating pressure of the prefractionation column;
   (d) vaporizing a first portion of the prefractionation columns bottoms stream by heat exchange with a low temperature fluid stream having a temperature of about 150-200° C. and passing the vaporized first portion to the prefractionation column; and
   (e) separating a second portion of the prefractionation column bottoms stream in a desorbent column to provide a desorbent column overhead stream rich in benzene and a desorbent column bottoms stream rich in the $C_{7+}$ aromatics.

17. The process of claim 16, wherein the prefractionation column is operated at a pressure of from about 100 to about 210 kPa.

18. The process of claim 16, wherein at least about 70 wt % of benzene present in the spent regenerant stream is separated into the prefractionation column overhead stream.

19. The process of claim 16, wherein the low temperature fluid stream is a selective dehydrogenation zone stripper bottoms stream.

* * * * *